United States Patent
Chandra et al.

(10) Patent No.: US 9,404,151 B2
(45) Date of Patent: Aug. 2, 2016

(54) NON CONTACT REAL TIME MICRO POLYMERASE CHAIN REACTION SYSTEM AND METHOD THEREOF

(75) Inventors: Swetha Chandra, Bangalore (IN); Sudip Mondal, Bangalore (IN); Venkataraman Venkatakrishnan, Karnataka (IN); Sathyadeep Viswanathan, Karnataka (IN); Renjith Mahiladevi Radhakrishnan, Karnataka (IN); Raviprakash Jayaraman, Karnataka (IN); Chandrasekhar Bhaskaran Nair, Karnataka (IN); Pillarisetti Venkata Subbarao, Karnataka (IN)

(73) Assignee: BIGTEC PRIVATE LIMITED, Rajajinagar, Bangalore (IN)

( * ) Notice: Subject to any disclaimer, the term of this patent is extended or adjusted under 35 U.S.C. 154(b) by 473 days.

(21) Appl. No.: 13/695,254

(22) PCT Filed: Apr. 28, 2011

(86) PCT No.: PCT/IB2011/051872
§ 371 (c)(1),
(2), (4) Date: Oct. 29, 2012

(87) PCT Pub. No.: WO2011/135535
PCT Pub. Date: Nov. 3, 2011

(65) Prior Publication Data
US 2013/0101983 A1    Apr. 25, 2013

(30) Foreign Application Priority Data
Apr. 30, 2010 (IN) .......................... 1215/CHE/2010

(51) Int. Cl.
*C12Q 1/68* (2006.01)
*B01L 7/00* (2006.01)
*C12Q 3/00* (2006.01)

(52) U.S. Cl.
CPC . *C12Q 1/686* (2013.01); *B01L 7/52* (2013.01); *C12Q 3/00* (2013.01); *B01L 2200/027* (2013.01); *B01L 2200/0684* (2013.01); *B01L 2200/147* (2013.01); *B01L 2300/0816* (2013.01); *B01L 2300/0887* (2013.01); *B01L 2300/12* (2013.01); *B01L 2300/1816* (2013.01)

(58) Field of Classification Search
CPC ..................................................... H05B 6/062
USPC .......................................................... 435/5
See application file for complete search history.

(56) References Cited

U.S. PATENT DOCUMENTS

2005/0158725 A1    7/2005  Yukimasa et al.
2008/0095679 A1*   4/2008  John Shigeura ............. 422/198
2008/0225290 A1*   9/2008  Wilson et al. ................ 356/317

OTHER PUBLICATIONS

Mondal S, Venkataraman V. Novel fluorescence detection technique for non-contact temperature sensing in microchip PCR. J Biochem Biophys Methods. Aug. 1, 2007; 70(5):773-7. Epub May 8, 2007.*
Ahmad F, Hashsham SA. Miniaturized nucleic acid amplification systems for rapid and point-of-care diagnostics: a review. Anal Chim Acta. Jul. 6, 2012; 733:1-15. Epub May 3, 2012. Review.*
Baek, S. K., Min, J., & Park, J. H. (2010). Wireless induction heating in a microfluidic device for cell lysis. Lab on a Chip, 10(7), 909-917.*
Pal, D., & Venkataraman, V. (2002). A portable battery-operated chip thermocycler based on induction heating. Sensors and Actuators A: Physical, 102(1), 151-156.*
Baek, S., et al, "Wireless induction heating in a microfluidic device for cell lysis," Lab on a Chip, vol. 10, pp. 909-917, published Jan. 19, 2010 Abstract, p. 909, col. 1, paragraph 1 & p. 910 & p. 912, section 2.7 & p. 913, col. 2, paragraph 2 & p. 916, col. 2, paragraph 3 & Figure 1(a).
Pal, D., et al, "A portable battery-operated chip thermocycler based on induction heating," Sensors and Actuators, A 102, pp. 151-156, 2002 Abstract, section 1, paragraphs 1 & 3, section 2.1, p. 153, col. 1, paragraph 1 & 3, Figure 2.
Xiang, Q., et al, "Miniature real time PCR on chip with multi-channel fiber optical fluorescence detection module," Biomedical Microdevices, vol. 9, No. 4, pp. 443-449, 2007 Whole document.
Lee, S. H., et al., "A polymer lab-on-a-chip for reverse transcription (RT)-PCR based point-of-care clinical diagnostics", Lab on a Chip, vol. 8, pp. 2121-2127, published Oct. 31, 2008 Whole document.
International Search Report for PCT/IB2011/051872, ISA/AU, mailed Jul. 15, 2011, and International Preliminary Report on Patentability, IPEA/AU, mailed Mar. 21, 2012.

* cited by examiner

*Primary Examiner* — Angela M Bertagna
*Assistant Examiner* — Olayinka Oyeyemi
(74) *Attorney, Agent, or Firm* — Harness, Dickey & Pierce, P.L.C.

(57) ABSTRACT

The present disclosure provides a non-contact real time micro Polymerase Chain Reaction (PCR) system comprising; a chip having a reaction chamber for holding a sample and an embedded metal heater below the reaction chamber for heating the sample; an optical unit comprising an associated LED driver and a photo detector amplifier placed above the chip to detect fluorescence; an induction heater mounted around the chip and inductively coupled to the metal heater; an infrared temperature sensor mounted below the chip for measuring a temperature of the metal heater, wherein the infrared temperature sensor is interfaced with a signal conditioner; and a controller interfaced with the signal conditioner and the induction heater for regulating the power to the induction heater based on feedback received from the infrared temperature sensor through the signal conditioner.

16 Claims, 8 Drawing Sheets
(4 of 8 Drawing Sheet(s) Filed in Color)

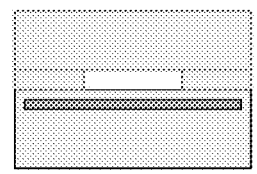
FIG. 2a          FIG. 2b          FIG. 2c
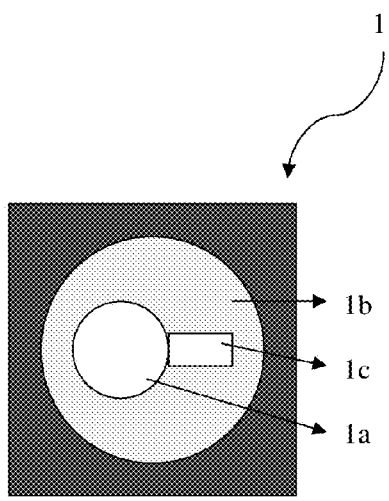
FIG. 2d
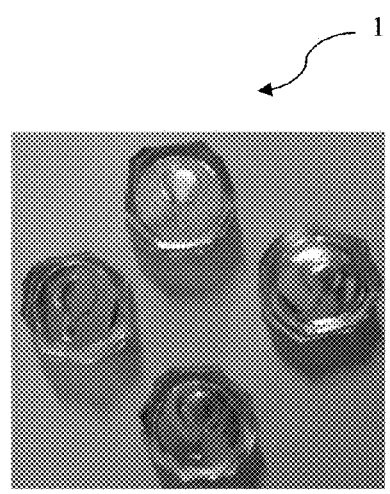
FIG. 2e

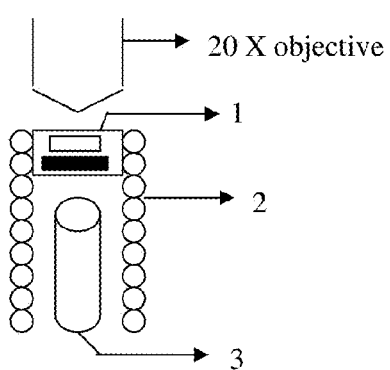 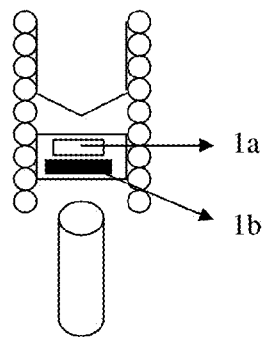 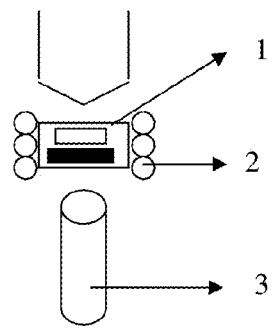
FIG. 3a  FIG. 3b  FIG. 3c
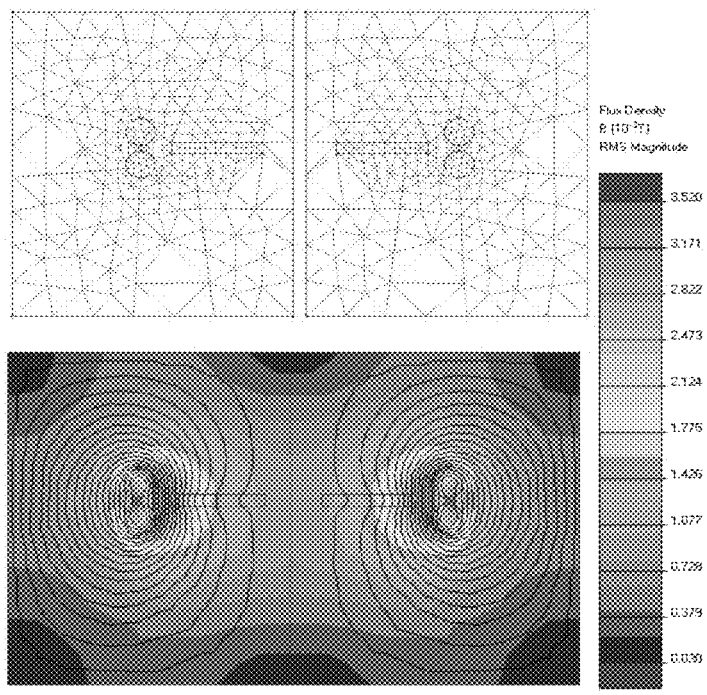
FIG. 4

NON CONTACT REAL TIME MICRO POLYMERASE CHAIN REACTION SYSTEM AND METHOD THEREOF

CROSS REFERENCE TO RELATED APPLICATIONS

This application is a 371 U.S. National Stage of International Application No. PCT/IB2011/051872, filed Apr. 28, 2011 and published in English as WO 2011/135535, on Nov. 3, 2011. This application claims priority to Indian Patent Application No. 1215/CHE/2010, filed Apr. 30, 2010. The disclosures of the above applications are incorporated herein by reference.

REFERENCE TO A SEQUENCE LISTING

The material in the ASCII text file entitled "Sequence Listing_ST25.txt" is hereby incorporated by reference in its entirety. The ASCII text file entitled "Sequence Listing_ST25.txt" was created on Dec. 11, 2012 and the size is 736 bytes.

TECHNICAL FIELD

Embodiments of the present disclosure relates to a non-contact real-time micro-Polymerase Chain Reaction (PCR) system, more particularly embodiments relates to a PCR system having inductively heated chip with sealed reaction chamber and infrared temperature sensing.

BACKGROUND OF THE DISCLOSURE

In molecular biology, PCR is a technique to amplify a single or few copies of a piece of Deoxyribonucleic Acid (DNA) by several orders of magnitude, generating millions of copies of a particular DNA sequence. This method is based on thermal cycling, i.e. continuous heating and cooling of the sample. As PCR progresses, the DNA generated is itself used as a template for replication. PCR involves three major steps of heating and cooling that is repeated for 25-30 times. Each cycle comprises of (i) denaturation at ~94 degrees when all the double strands melt into single stranded DNA, (ii) annealing at lower temperature ~54 degrees when both the primers pair up with single stranded templates and (iii) extension at ~72 degrees where the polymerase extends the primer by attaching the bases complementary to the template, thus making two copies of double stranded DNA for each template.

The conventional bench-top PCR systems use large metal heating and cooling blocks that cycle the temperature of samples loaded inside polypropylene tubes, the miniaturization of the reaction chamber offers advantage in terms of integration, speed and efficiency. With these advantages the development of miniaturized systems for PCR has become an area of active interest. Devices have been fabricated by many research groups using various materials that are suitable for biological reactions. Most of the research groups have been using silicon as their substrates for its high thermal conductivity and well characterized processing conditions. Bare silicon is not optically transparent and has been reported to inhibit PCR reactions. Oxidized silicon or glass is preferable, but the complex multi-step fabrication of the reaction chambers, heaters and temperature sensors in these chips makes them too expensive for single-use disposable applications. In addition, a reaction chamber sealing step is required to avoid thermal evaporation, which is typically carried out by one of the different types of bonding such as fusion bonding, anodic bonding, adhesive bonding, reversible bonding and ultrasonic bonding. On the other hand, polymers are bio-compatible low cost materials which are transparent and can be easily molded at lower temperatures. Their thermal conductivity, however, compared to silicon, is much lower. Therefore the design of heaters and temperature sensors is important.

The choice of heating method plays an important role along with the choice of material for fast microchip PCR protocols. There have been generally two types of heating methods commonly used by various groups: contact and non contact heating. The contact heating method utilizes a resistive heater to heat up the PCR solution. The heaters are typically a thin film metal, mostly Platinum (Pt) due to its reproducible temperature dependence of resistance, ability to withstand high temperature, good chemical stability and high purity. In addition a thin layer of titanium is often used as an adhesive layer for Pt, since the latter exhibits a high diffusion rate at high temperature, which will deteriorate its performance. However Pt is very expensive and optically opaque. Other metals and alloys have also been used as heaters. Some commercially available peltier block thermo-electric units have also been widely used in temperature control of PCR chips in spite of their larger thermal mass, slower temperature ramping rates and being non transparent. Most commonly used non contact heating schemes for PCR are based on hot air cycling which is carried out by rapidly switching streams of air at the desired temperature. However the control and application of hot air for single chips may not be easy. In some reports, infrared radiation using a tungsten lamp was utilized as a non contact source of heating which needed less than 15 min for 35 cycles. However the tungsten lamp is a non-coherent and non-focused light source, and therefore needs high power (50 to 100 W) for the chip to reach the required temperature. In another report, an inexpensive halogen lamp as a low power radiation source for rapid temperature ramping in silicon micro-reaction chambers was described.

In light of forgoing discussion, it is necessary to develop non-contact real-time micro-Polymerase Chain Reaction (PCR) system which has inductively heated polymer and cite chip made of a material selected from group comprising but not limited to Poly-Dimethyl-Siloxine [PDMS], acrylic, polypropylene and polycarbonate with sealed reaction chamber and infrared temperature sensing to overcome the above mentioned problems.

OBJECTS OF THE DISCLOSURE

One object of the present disclosure is to provide a non-contact real-time micro-Polymerase Chain Reaction (PCR) system having an induction heater and infrared radiation temperature sensor.

One object of the present disclosure is to provide a non-contact real-time micro Polymerase Chain Reaction (PCR) system having a chip with a reaction chamber and an embedded metal heater.

SUMMARY OF THE DISCLOSURE

The shortcomings of the prior art are overcome and additional advantages are provided through the provision of a system and method as claimed in the present disclosure.

Additional features and advantages are realized through the techniques of the present disclosure. Other embodiments and aspects of the disclosure are described in detail herein and are considered a part of the claimed disclosure.

The principal embodiment of the present disclosure provides a non contact real time micro Polymerase Chain Reaction [PCR] system. The system includes a chip having a reaction chamber for holding a sample and an embedded metal heater below the reaction chamber for heating the sample. An optical unit comprising associated LED driver and photo detector amplifier placed above the chip to detect the fluorescence. An induction heater mounted in around the chip and is inductively coupled to the metal heater. An infrared temperature sensor mounted below the chip for measuring a temperature of the metal heater, wherein said infrared temperature sensor is interfaced with a signal conditioner. And a controller interfaced with the signal conditioner and the induction heater for regulating the power to the induction heater based on feedback received from the infrared temperature sensor through the signal conditioner.

In one embodiment of the present disclosure, the chip is fabricated from a material selected from a group but not limited to poly-dimethyl-siloxane [PDMS], acrylic, polycarbonate, polypropylene.

In one embodiment of the present disclosure the LED driver and photo detector amplifier and the pulse width module controller are interfaced with the data acquisition and control system to monitor different parameters of PCR.

In one embodiment of the present disclosure the induction heater is a coil, said coil is positioned proximal to the chip for inductively heating the metal heater. And the distance between the chip and coil varies between 0-10 mm.

In one embodiment of the present disclosure, the controller (5) is selected from at least one of pulse width modulator, Proportional Integral Differential (PID) controller and ON/OFF switch.

In one embodiment of the present disclosure, the reaction chamber has a nozzle on one side to confine a trapped air during filling of the sample.

Another embodiment of the present disclosure provides a method of operating a non contact real time micro Polymerase Chain Reaction [PCR] system. The method comprises acts of filling sample into a reaction chamber of a chip. The sample is heated using an embedded metal heater, wherein said embedded metal heater is inductively coupled to a induction heater for receiving the heat energy from the induction heater. Then temperature of the metal heater is measured using an infrared temperature sensor. And a power to the induction heater is regulated using controller based on feedback received from the infrared temperature sensor.

In one embodiment of the present disclosure, a trapped air is flushed out from the reaction chamber through nozzle provided at one end of the chip before filling the sample.

In one embodiment of the present disclosure, florescence is detected using optical unit comprising associated LED driver and photo detector amplifier.

In one embodiment of the present disclosure, monitoring different parameters of polymerases chain reaction using data acquisition and control system.

In one embodiment of the present disclosure, supplying heat by electromagnetic induction process from induction heater to the metal heater.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF ACCOMPANYING DRAWINGS

"The patent or application file contains at least one drawing executed in color. Copies of this patent or patent application publication with color drawings will be provided by the Office upon request and payment of necessary fee."

The novel features and characteristic of the disclosure are set forth in the appended claims. The disclosure itself, however, as well as a preferred mode of use, further objectives and advantages thereof, will best be understood by reference to the following detailed description of an illustrative embodiment when read in conjunction with the accompanying figures. One or more embodiments are now described, by way of example only, with reference to the accompanying figures wherein like reference numerals represent like elements and in which:

FIGS. 2a-2c illustrates three step fabrication processes for the PDMS chip with embedded heater and reaction chamber.

FIGS. 2d and 2e illustrates a top view and perspective view of the PDMS chip.

FIGS. 3a-3c illustrates position of the coil with respect to the chip, objective lens and IR sensor.

FIG. 4 illustrates the 2D numerical simulation of the magnetic field lines around an 8 mm diameter nickel ring of thickness 0.4 mm which is inductively heated using a 2 turn 10 mm dia copper coil of wire diameter 1 mm carrying current of 10 A at frequency 50 kHz.

Figure 5:
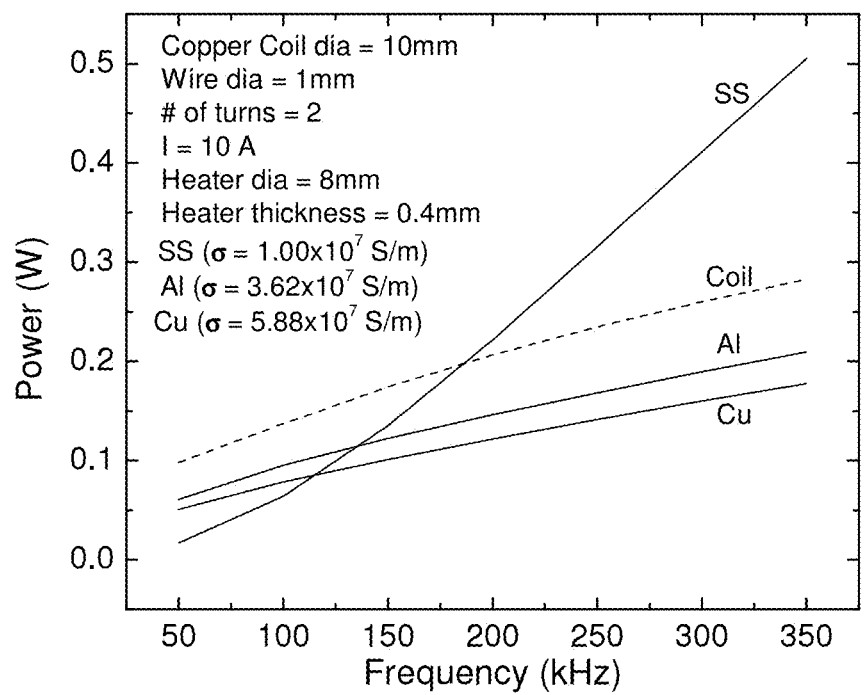

FIG. 5 illustrates numerical simulations of power dissipated in different heater materials: Stainless steel (SS), Aluminum (Al) and Copper (Cu) as a function of frequency. Also shown is power dissipated in the copper coil itself (Coil).

Figure 6:
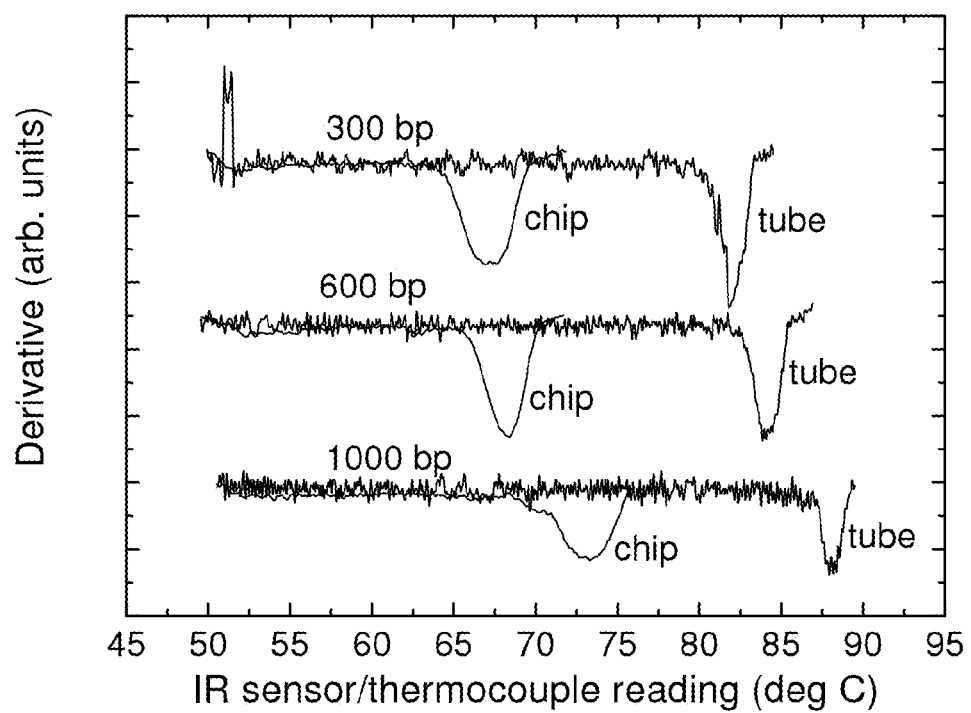

FIG. 6 illustrates melting curves showing the derivative of the real time fluorescence signal as a function of the temperature (uncalibrated IR sensor reading for the chip and calibrated thermocouple for the tube inside MJR thermocycler).

Figure 7:
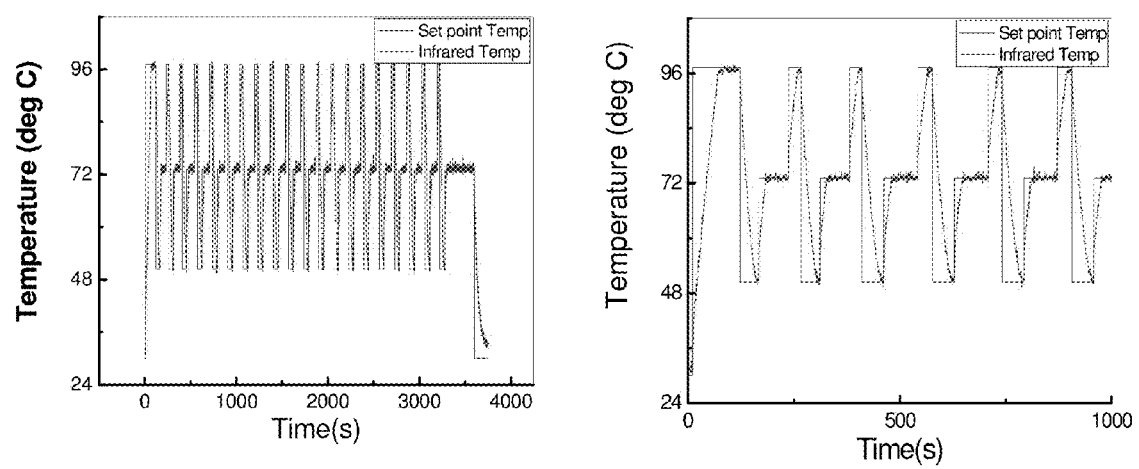

FIG. 7 illustrates temperature profile during cycling. The black line shows the setpoints switched instantaneously by the computer while the red curve shows the (corrected) temperature from the IR sensor. The figure on the left shows the complete profile for all cycles while the right panel shows the first few cycles.

Figure 8:
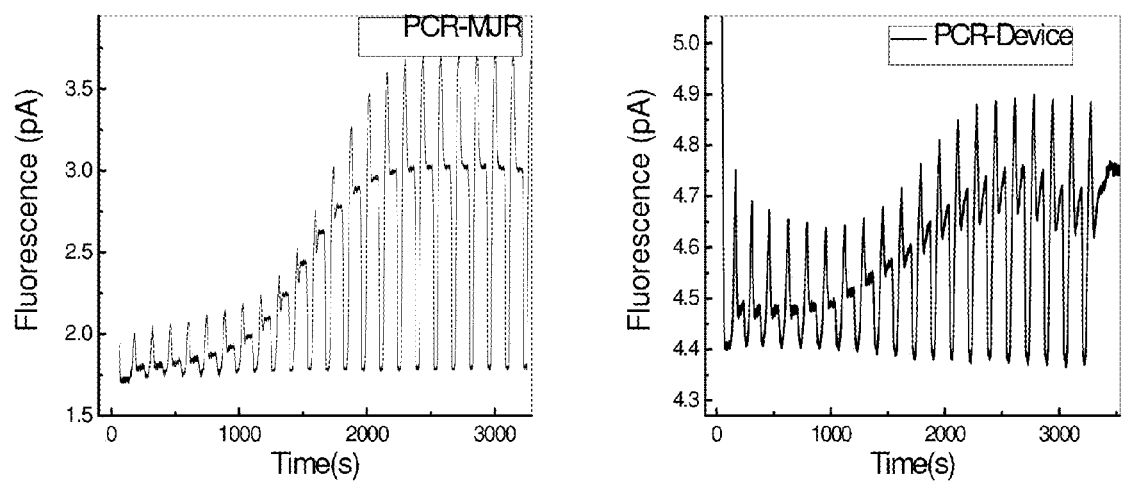

FIG. 8 illustrates the real time fluorescence signal from amplification of 300 bp lambda DNA in the PDMS chip along with a similar experiment performed in polypropylene tubes using the commercial thermocycler.

Figure 9:
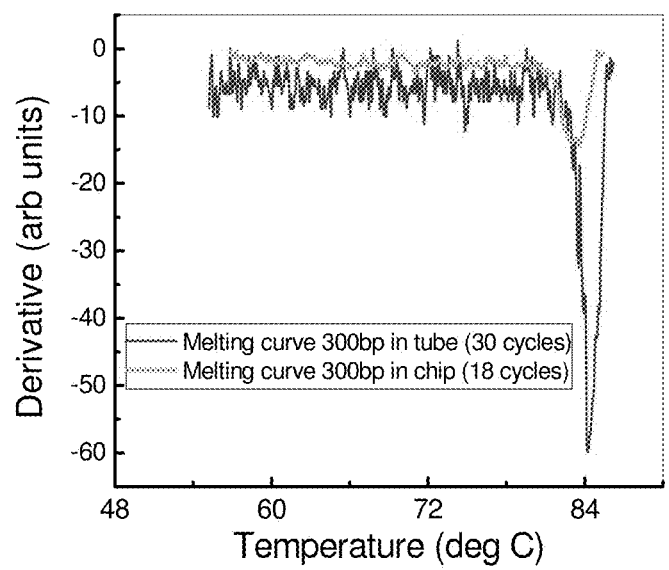

FIG. 9 illustrates shows melting curve analysis of 300 bp DNA amplified in tube and PDMS chip. Both samples were loaded in the chips to record the melting curves with the IR sensor.

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

The foregoing has broadly outlined the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

To overcome the problems as discussed hereinabove, the present disclosure provides a non-contact real time micro Polymerase Chain Reaction system (A). The system includes an induction heater (2) which is simple and does not require any light radiation and additional lenses and filters. The induction heating leads to much simpler chip (1) fabrication steps with improved reliability. Further an infrared temperature sensor (3) is used in the system to monitor and control the chip temperature. This obviates the need for contact type thermometers such as thermocouples or resistors which have to be embedded into the chip using complex fabrication steps. Since the thermometer is not part of the chip (1) itself, the cost and disposability of the chip is vastly improved. Further, thermometer calibration has to be done only once as part of the chip reader unit and not for every chip. The use of non-contact temperature sensing in addition to the heating is essential to realize fully the advantages of a complete non-contact PCR chip system.

The present disclosure provides the design of a completely non-contact PCR system (A) using a PDMS chip (1). Non-contact heating is realized using electromagnetic induction whereas non-contact temperature sensing is accomplished with an infrared thermocouple (4). The disclosure more particularly relates to a design of chip (1) with embedded heater (1b), optimization of choice of heater metal and its geometry, use of infrared temperature sensing (3) to monitor temperature, optimization of heater surface coatings for best infrared emission and fluorescence, use of DNA melting curves to calibrate the infrared thermometer, a sealed reaction chamber (1a) inside the PDMS chip (1) into which samples can be injected using a micro-syringe which obviates the need for mineral oil or other additives as evaporation barriers, a fabrication process for the heater (1b) and reaction chamber (1a) parts and bonding them together using plasma bonding in air, a resonantly excited induction coil whose frequency is tuned for optimum power transfer to the embedded heater (1b), and finally a low power pulse width modulation (PWM) controller (5) for regulating the power to the induction heater (2) based on feedback from the infrared temperature sensor (3).

A prototype of the non-contact PCR system (A) including fluorescence detection unit has been built and tested with amplification and melting of lambda DNA. The PCR instrument of the instant disclosure measures fluorescence at every 0.5 seconds during PCR. The instant disclosure demonstrates the amplification of lambda DNA of including but not limiting to sizes 600, 800 and 1000 bp, and verified the product specificity with melting curves compared with commercial PCR machines. The use of a disposable transparent biocompatible polymer chip without any electrical contacts for real time microchip PCR applications can pave the way for rapid deployment of these low-cost systems in the field for a variety of applications.

Figure 1:
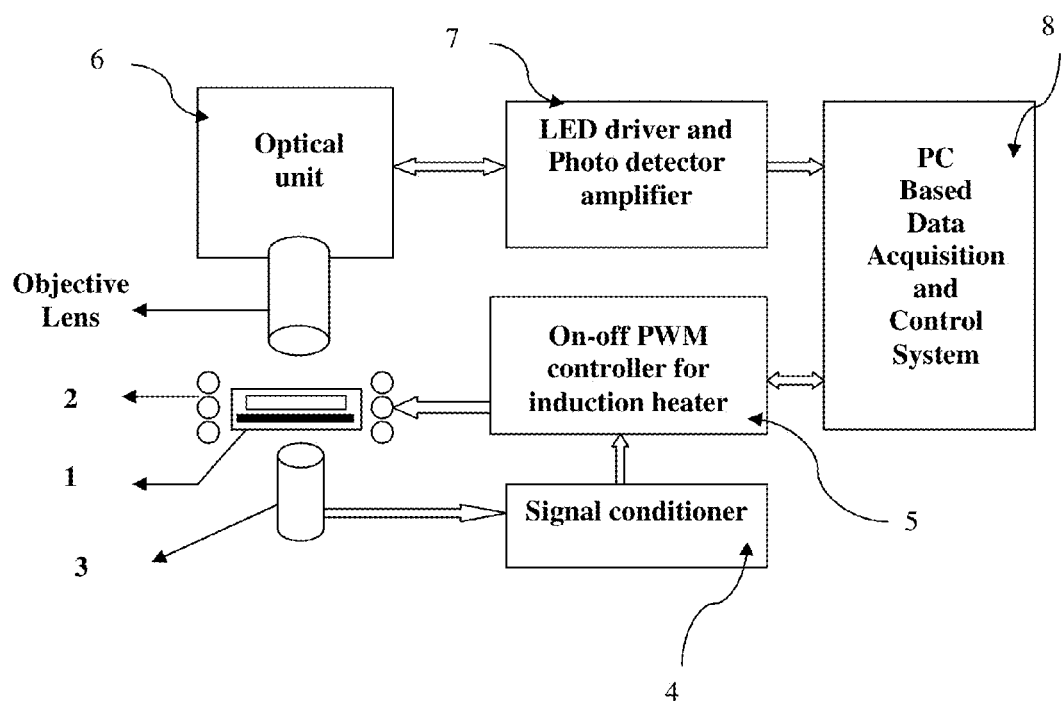
FIG. 1 illustrates block diagram of the non-contact micro-PCR system.

Methods and Materials:

FIG. 1 is an exemplary embodiment which illustrates of the non-contact micro-PCR system (A). The system comprises PDMS chip (1) with an embedded metal heater (1b) which is inductively coupled to an induction heater (2). The infrared radiation temperature sensor (3) measures the heater (1a) temperature from bottom of the chip (1). The temperature signal is compared with the set point and the power to the induction heater (2) is regulated by means of a PWM on-off control circuit (5). An optical pick-up unit (6) with associated LED driver and photo detector amplifier (7) is positioned above the chip (1a) to detect the fluorescence. The photo detector amplifier (7) and PWM on-off control circuit (5) are interfaced with a data acquisition and control system (8). The said data acquisition and control system (8) has a built in program which monitors parameters of polymerases chain reaction. Further details of the individual sub-systems are given below.

Fabrication of the PDMS Chip

FIGS. 2a-2c are exemplary embodiments which illustrates the steps involved in fabrication of PDMS chip (1). The upper half of the chip (1) consists of the reaction chamber (1a) which was fabricated using the replica molding technique. The master was first designed and fabricated using SU-8 and photolithography. Negative photo resist [SU8 2150] was spin coated on a two inch silicon wafer at 1000 rpm for 30 seconds. After soft bake, the pattern on the photo-mask was transferred to the SU8 coated silicon wafer by UV exposure for two minutes. The exposed pattern was post baked, developed for 30 minutes and then hard baked. To obtain the upper half of the chip (1), 10:1 PDMS was poured on the master, baked and peeled off. The volume of reaction chamber (1a) is about 5 μL [~3 mm diameter and 600 μm height]. The circular chamber has a nozzle (1c) on one side to confine the trapped air during filling. The bottom half of the chip (1) consisted of a thin circular metal sheet embedded in PDMS. This was fabricated by simply immersing the metal discs into a thin layer of PDMS poured on a hydrophobic glass slide. After hard baking for 2 hours at 90 degrees Celsius, the pieces were cut and peeled off from the slide. Finally, the upper and lower PDMS halves were exposed to air plasma for 2 minutes, placed in contact under mild pressure, and heated in the oven for 30 minutes at 90 degrees Celsius to obtain the irreversibly bonded PCR chip (1) with embedded reaction chamber (1a) and heater (1b).

In order to use the chip (1), the reaction chamber (1a) is first punctured at the nozzle (1c) using a micro-syringe. This is followed by filling the chamber (1a) with the solution using the micro-syringe from the opposite side. Most of the air is displaced towards the nozzle (1c) and escapes from the punctured vent. Any remaining trapped air bubble is confined in the nozzle (1c) and does not interfere with the PCR or the fluorescence signal.

FIGS. 2d and 2e illustrates top view and perspective view of the PDMS chip (1) respectively. The chip (1) includes a reaction chamber (1a) for holding the sample and an embedded metal heater (1b) below the reaction chamber (1a) for heating the sample. The chip (1) further comprises a nozzle (1c) at the side of the reaction chamber (1a) to flush out the entrapped air from the reaction chamber (1a).

Embedded Heater Design

For a given primary coil, the power coupled to the secondary depends on the frequency, resistivity of the metal and geometrical dimensions (diameter and thickness). Larger dimensions will improve the power coupled, but degrades the passive cooling rate due to increased thermal mass. Higher frequencies will lead to better heating efficiency, but this has to be traded off with switching losses in the power transistors. The different commercially available steel, copper and aluminium metal sheets of varying thicknesses are tried, simulations were carried out to determine the best switching frequency. It is important that the top surface of the sheet is highly polished to improve the collected fluorescence signal while the bottom surface is coated black for the best thermal detection by the Infrared Radiation temperature sensor (3).

Induction Heating Coil and IR Detector

The infrared detector (3) has to be placed within ~2 mm to accurately sense the temperature of the emission surface of diameter ~7 mm. Therefore it is placed just below the chip (1).

Since the body of the sensor is metal, the location of the induction heater (2) primary coil is important. If a coil of 10 turns is used below the chip (1) as shown in FIG. 3a, the infrared temperature sensor (3) body also gets heated and disturbs the temperature signal. On the other hand, if the coil is placed above the chip (1) as shown in FIG. 3b, the objective lens (6) with the metal body gets heated and leads to excessive power dissipation. Further, handling of the chip (1) becomes inconvenient and there is loss of heating efficiency. Therefore the final optimized design as shown in FIG. 3c consisted of a coil of 3 turns placed just around the chip (1) and away from the optical unit (6) and IR sensor (3). The induction heating coil is placed proximal to the chip (1) and the distance between the induction coil and chip (1) varies from 0-10 mm.

Fluorescence Detection Unit

The fluorescence detection system optimized for the intercalating dye Sybr Green consists of a 470 nm blue LED excitation source, projected using a dichroic mirror and focused on the PDMS chip (1) using a 20× microscope objective. The emission at 520 nm was collected through the same lens, filtered using a band-pass filter, and focused on a silicon photo diode. The LED intensity was modulated at 190 Hz and the photo current was detected synchronously using a lock in amplifier. The signal acquired every second when plotted against the time yielded the continuous fluorescence emission during PCR.

Temperature Calibration

The commercial IR sensor has to be calibrated for the emissivity of the black painted embedded heater. In addition the reaction chamber (1a), which is located ~0.5 mm away from the heater (1b), will be at a lower temperature. Therefore the DNA itself used inside the reaction chamber (1a) as a temperature standard for calibration. This is done by identifying the melting point of the DNA inside the chip (1) using fluorescence, recording the IR sensor (3) signal at which this melting occurs, and comparing that with the actual melting point obtained in a commercial PCR thermocycler. By using DNA with different melting points, the sensor reading can be calibrated to the actual chamber temperature. For a given system (A) this has to be done only once, since subsequent reactions take place inside similar chips (1) place at the same location with respect to the sensor.

Signal Processing and Power Control Electronics

The DC signal from the infrared radiation temperature sensor (3) was buffered using a precision op-amp and amplified using the thermocouple amplifier IC with cold junction compensation from Analog Devices. The signal was fed into the built-in comparator of the microcontroller which also generates the PWM waveform. The set temperature from the PC was also fed to the comparator using a USB DAC/ADC system. The comparator output is controlled by the MOSFET driver and said output is sent to in the form of PWM signal to the power MOSFET. Then the transistor is switched on, and power from a 5 Volt DC supplied into a resonant circuit formed by the induction heater primary coil and a 10 µF low loss capacitor. The USB-DAQ system records the IR temperature signal on the PC as well as the fluorescence signal from the optical unit.

Sample Preparation

PCR sample preparation was done using 2X DyNAmo Sybr green Master mix, Taq polymerase, Lambda DNA, PCR water and the Primers. A 50 microliter mix was prepared with 1 microliter of lambda DNA template, 2.5 microliter of P1 [5-AGT GTCGAA TTC TGA TCG TGG TGA TAT CCG-3] (SEQ ID NO:1), 2.5 microliter of P2 [5-AGT GTC AAG CCT CAG CTT CAG TTC TCT-3] (SEQ ID NO:2), 1 microliter of Taq polymerase, 25 microliter of Master mix, and 18 microliter PCR water to produce 311 by amplified DNA. Different primers were used to produce ~600 by and ~1000 by of amplified lambda DNA.

Step Wise Execution of Non-Contact PCR

The non-contact real-time PCR system (A) uses a sealed disposable PDMS chip (1) with embedded metal heater (1b) to run a PCR reaction, the following steps have to be executed:

a. The PCR sample is prepared according to the normal bench-top commercial thermocycler protocols. Sample contains template DNA, primers, dNTPs, Taq polymerase or equivalent, appropriate salts and buffers in PCR water. Sample also contains Sybr Green or Taqman fluorescence probes. Commercial master mixes such as DyNAmo kit and its equivalents can be used.

b. The reaction chamber (1a) is punctured at the nozzle (1c) using a clean and sterilized syringe with fine needle to release trapped air. This step is optional since in some cases the air bubble does not interfere with the reaction.

c. The sample about 5 to 10 microliters is injected to the reaction chamber (1a) of the PDMS chip (1) by puncturing through the top sealing. During this process the trapped air is pushed towards the nozzle (1c) which escapes through the punctured hole from step 2. Any remaining trapped air forms a small bubble in the notch and does not interfere with the PCR reaction subsequently.

d. The PDMS chip (1) with the PCR sample is placed on a small holder inside the coil of the induction heater (2). The holder position is pre-adjusted for optimum heating and fluorescence and need not be disturbed for any reaction.

e. The optical head is lowered into position for collecting the fluorescence. The position of the head is pre-adjusted for maximum fluorescence and need not be disturbed for any reaction.

f. In some designs, the optical head is fixed whereas the sample holder can be moved for placing and removing the chip (1). In the final position, the optical lens is a few millimeter away from the PDMS surface.

g. The infrared radiation temperature sensor (3) is located at a pre-adjusted position below the sample holder and need not be disturbed for any reaction. The sample holder has a center hole through which the infrared radiation is collected by the sensor.

h. After the PDMS chip (1) and optical head (6) is placed in position, a command is given to the microcomputer to execute the software controller. The parameters of the reaction i.e. initial incubation temperature and time, number of cycles with respective temperature and time for denaturation, annealing and extension steps, and final extension temperature and time, are also entered into the software. The software then issues commands to the hardware which controls the temperature and time for each step. The fluorescence is recorded either continuously or at user-determined times during each cycle.

i. After the reaction, the sample cools to room temperature. The PDMS chip (1) can now be removed from the holder.

j. The data of fluorescence and temperature as a function of time can be retrieved from the software and analyzed.

Results

The magnetic flux density generated by a small coil around a thin metal plate as determined by QuickField 2-D electromagnetic simulator is shown in the FIG. 4.

For the simulations, the coil consisted of two wire 10-mm diameter loop with 1-mm diameter copper wire of conductivity $5.88 \times 10^7$ S/m. The heater was a 8 mm diameter 0.4 mm thick Nickel disc of conductivity $1 \times 10^7$ S/m and the frequency was 50 KHz. Apart from the magnetic field, the power dissipated in the copper coil (primary) and the heater disc (secondary) was also calculated for different heater materials i.e. stainless steel (SS), aluminium (Al) and Copper (Cu) as a function of frequency as shown in FIG. 5.

It is observed that the power dissipated in the primary (Coil) is relatively independent of the material and increases with frequency. On the other hand, the power dissipated in the heater is largest for Al at low frequencies and stainless steel (SS) at higher frequencies. However the power dissipated in the switching transistors increases at higher frequencies and therefore an optimum frequency of ~130 KHz with Aluminum heater (which has similar conductivity to copper but better fluorescence reflection from its polished surface) was chosen for the PCR experiments. The optimized heater geometry consisted of an Al sheet of thickness 0.38 mm, diameter 7.14 mm and black painted on the bottom side for highest infrared emissivity.

The temperature calibration was carried out by comparing the melting curves of three different DNA viz lambda 300 bp, 600 bp and 1000 bp in the chip (1) and in polypropylene tubes loaded in a commercial thermocycler from MJ Research USA. About 5 microliter was loaded and the temperature ramped from annealing (54 deg) to denaturation (90 deg).

FIG. 6 shows the melting curves obtained and Table 1 compares the IR sensor (3) reading at the melting point of the DNA inside the PDMS chip (1) with the actual melting point as read from the commercial thermocycler.

TABLE 1

Melting points from tube (calibrated thermocouple) and chip (uncalibrated IR sensor) for different lambda DNA samples.

| Lambda DNA | Melting curve in tube | Melting curve in chip |
|---|---|---|
| 300 | 81 | 67 |
| 600 | 83.5 | 68.4 |
| 1000 | 88.5 | 73 |

A linear fit between the two established the calibration curve and the IR sensor (3) reading were corrected to display the true temperature of the sample inside the reaction chamber (1a) for the subsequent PCR experiments. The PCR protocol for 5 μL loaded in the chip consisted of an initial denaturation step at 96 deg for 60 sec followed by denaturation (96 deg for 15 sec), annealing (48 deg for 15 sec), and extension (72 deg for 100 sec) steps for 18 cycles and final extension at 72 deg for 300 sec. FIG. 7 shows the temperature profile maintained by on-off heater control with feedback from the non-contact IR sensor (3). Note that a small ~5 W fan was used to improve the cooling rate when switching between denaturation and annealing steps.

FIG. 8 shows the real time fluorescence signal from amplification of 300 bp lambda DNA in the PDMS chip along with a similar experiment performed in polypropylene tubes using the commercial thermocycler.

Amplification could be reproducibly obtained for all the DNA samples (300 bp, 600 bp and 1000 bp). After amplification, a melting curve analysis was performed in the same chip as shown in FIG. 9. Also shown is a melting curve obtained from a similar DNA sample loaded in another PDMS chip, but which was amplified in a tube using the commercial thermocycler. The two melting runs in PDMS devices were almost identical with minor differences due to the different cycle numbers.

INDUSTRIAL APPLICABILITY

The present disclosure has wide application in Bio-MEMS field, namely, DNA amplification using Polymerase Chain Reaction (PCR). DNA amplification is used in various forms for pathogen detection, forensic investigation, bio-defense, food and water control, environmental monitoring, DNA sequencing etc.

equivalents

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that

The invention claimed is:

1. A non-contact real time micro Polymerase Chain Reaction [PCR] system comprising;
   a chip having a reaction chamber for holding a sample and an embedded metal heater below the reaction chamber for heating the sample;
   an optical unit comprising an associated LED driver and photo detector amplifier placed above the chip to detect fluorescence;
   an induction heater mounted around the chip and is inductively coupled to the metal heater, wherein the induction heater is a coil;
   an infrared temperature sensor mounted below the chip for measuring a temperature of the metal heater, wherein the infrared temperature sensor is interfaced with a signal conditioner; and
   a controller interfaced with a signal conditioner and the induction heater for regulating the power to the induction heater based on feedback received from the infrared temperature sensor through the signal conditioner.

2. The system as claimed in claim 1, wherein the chip is fabricated from a material selected from at least one of polydimethyl-siloxane (PDMS), acrylic, propylene and polycarbonate.

3. The system as claimed in claim 1, wherein the LED driver and photo detector amplifier and the controller are interfaced with a data acquisition and control system to monitor different parameters of PCR.

4. The system as claimed in claim 1, wherein the controller is selected from at least one of pulse width modulator, Proportional Integral Differential (PID) controller and ON/OFF switch.

5. The system as claimed in claim 1, wherein the reaction chamber has a nozzle on one side to confine a trapped air during filling of the sample.

REFERRAL NUMERALS

| Reference number | Description |
| --- | --- |
| A | PCR system |
| 1 | PDMS chip |
| 1a | Reaction chamber |
| 1b | Metal heater |
| 1c | Nozzle |
| 2 | Induction heater |
| 3 | Infrared temperature sensor |
| 4 | Signal conditioner |
| 5 | PWM controller |
| 6 | Optical unit |
| 7 | LED driver and Photo detector amplifier |
| 8 | Data Acquisition and Control System |

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: 5' - 3' PCR Primer P1
<220> FEATURE:
<221> NAME/KEY: primer_bind
<222> LOCATION: (1)..(30)

<400> SEQUENCE: 1
agtgtcgaat tctgatcgtg gtgatatccg        30

<210> SEQ ID NO 2
<211> LENGTH: 27
<212> TYPE: DNA
<213> ORGANISM: Artificial Sequence
<220> FEATURE:
<223> OTHER INFORMATION: 5' - 3' PCR Primer P2
<220> FEATURE:
<221> NAME/KEY: primer_bind
<222> LOCATION: (1)..(27)

<400> SEQUENCE: 2
agtgtcaagc ctcagcttca gttctct        27

6. The system as claimed in claim 5, wherein the chip further comprises a vent, the vent being formed by puncturing the chip at the nozzle with a micro-syringe.

7. The system as claimed in claim 1, wherein the metal heater comprises a bottom surface that is coated black.

8. A system as claimed in claim 1 adapted for BIO-MEMS applications or adapted for DNA amplification.

9. The system as claimed in claim 1, wherein the coil is positioned at a distance between 0 mm to 10 mm from the chip for inductively heating the metal heater.

10. The system as claimed in claim 1, wherein the infrared temperature sensor is mounted within about 2 mm below the chip.

11. The system as claimed in claim 1, wherein the coil is a coil of three turns such that the coil is mounted around the chip and not around the optical unit or the infrared temperature sensor.

12. A method of operating a non-contact real time micro Polymerase Chain Reaction (PCR) system, said method comprising acts of;
    filling sample into a reaction chamber of a chip;
    heating the sample using an embedded metal heater, wherein the embedded metal heater is inductively coupled to an induction heater which is mounted around the chip, for receiving heat energy from the induction heater, wherein the induction heater is a coil;
    measuring a temperature of the metal heater using an infrared temperature sensor, wherein the infrared temperature sensor is mounted below the chip; and
    regulating a power to the induction heater using a controller based on feedback received from the infrared temperature sensor.

13. The method as claimed as claim 12, wherein a trapped air is flushed out from the reaction chamber through nozzle provided at one end of the chip before filling the sample.

14. The method as claimed in claim 12, wherein florescence is detected using optical unit comprising associated LED driver and photo detector amplifier.

15. The method as claimed in claim 12, further comprising monitoring different parameters of polymerase chain reaction using a data acquisition and control system.

16. The method as claimed in claim 12, wherein the induction heater supplies heat to the metal heater by an electromagnetic induction process.

* * * * *